United States Patent [19]

Edgren

[11] Patent Number: 4,522,625
[45] Date of Patent: Jun. 11, 1985

[54] DRUG DISPENSER COMPRISING WALL FORMED OF SEMIPERMEABLE MEMBER AND ENTERIC MEMBER

[75] Inventor: David Edgren, El Granada, Calif.

[73] Assignee: Alza Corporation, Palo Alto, Calif.

[21] Appl. No.: 427,870

[22] Filed: Sep. 29, 1982

[51] Int. Cl.³ .............................. A61K 9/22; A61K 9/32
[52] U.S. Cl. ..................................... 604/892; 604/890; 424/19; 424/32
[58] Field of Search ............................. 604/890–893; 424/19, 20, DIG. 7, 31–35

[56] References Cited

U.S. PATENT DOCUMENTS

| | | | |
|---|---|---|---|
| 3,538,214 | 11/1970 | Polli et al. | 424/20 |
| 3,845,770 | 11/1974 | Theeuwes et al. | 128/260 |
| 3,916,899 | 4/1975 | Theeuwes et al. | 128/260 |
| 4,008,719 | 2/1977 | Theeuwes et al. | 128/260 |
| 4,036,227 | 7/1977 | Zaffaroni et al. | 128/260 |
| 4,036,228 | 7/1977 | Theeuwes | 128/260 |
| 4,083,949 | 4/1978 | Benedikt | 424/20 |
| 4,093,708 | 6/1978 | Zaffaroni et al. | 425/15 |
| 4,096,238 | 6/1978 | Zaffaroni et al. | 425/15 |
| 4,111,201 | 9/1978 | Theeuwes et al. | 128/260 |
| 4,135,514 | 1/1979 | Zaffaroni et al. | 128/260 |
| 4,142,526 | 3/1979 | Zaffaroni et al. | 604/891 |
| 4,415,547 | 11/1983 | Yu et al. | 424/20 |
| 4,438,091 | 3/1984 | Gruber et al. | 424/19 |

*Primary Examiner*—Richard J. Apley
*Assistant Examiner*—Gregory Beaucage
*Attorney, Agent, or Firm*—Paul L. Sabatine; Edward L. Mandell; Steven F. Stone

[57] ABSTRACT

An osmotic dispenser is disclosed for releasing drug formulation in the gastrointestinal tract. The dispenser comprises a semipermeable-enteric wall surrounding a compartment housing drug formulation. A passageway in the wall communicates with the compartment for dispensing drug formulation.

2 Claims, 6 Drawing Figures

DRUG DISPENSER COMPRISING WALL FORMED OF SEMIPERMEABLE MEMBER AND ENTERIC MEMBER

FIELD OF THE INVENTION

This invention pertains to both a novel and useful osmotic dispenser for dispensing a beneficial agent to an environment of use. More particularly, the invention relates to a wall comprising a semipermeable member and an enteric member for regulating the agent release from the dispenser in the environment of use. The invention concerns also a composition comprising a semipermeable member and an enteric member.

BACKGROUND OF THE INVENTION

Osmotic therapeutic dispensers for the precision administration of drugs with control of their delivery patterns and with extended delivery times are known in U.S. Pat. No. 3,845,770 issued to patentee Theeuwes and Higuchi, and in U.S. Pat. No. 3,916,899 issued to the same patentee. The dispensers disclosed in these patents are made of a semipermeable wall that surrounds a compartment containing a drug. The semipermeable wall is permeable to the passage of an external fluid, impermeable to the passage of drug, and it has a portal for dispensing drug from the dispenser.

In U.S. Pat. Nos. 4,036,227; 4,093,708; 4,096,238; 4,135,54; and 4,142,526, all issued to patentee Zaffaroni, Michaels, and Theeuwes, an improvement is disclosed in the osmotic dispensers of U.S. Pat. Nos. 3,845,770 and 3,916,899. The improvement comprises an enteric layer, which does not disintegrate in the stomach but disintegrates in the intestine, coated onto the exterior surface of the semipermeable wall of the dispenser. The dispenser coated entirely with the enteric layer releases drug only in the intestine, and not in the stomach.

The above dispensers represent an outstanding and a pioneer advancement in the osmotic dispensing art, and they are useful for dispensing innumerable drugs to the environment of use. Now, it has been found the dispenser can be unexpectedly improved leading to more desirable results. For example, it will be appreciated by those versed in the dispensing art that if a novel and useful dispenser is made available for delivering drug at a rate or rates precisely controlled by the dispenser which rate or rates are in response to the biological environment within which it functions, such a dispenser would have a positive clinical value, and also represent a substantial contribution in the dispensing art.

OBJECTS OF THE INVENTION

Accordingly, it is an immediate object of this invention to provide a novel osmotic dispenser for dispensing a beneficial agent to produce a beneficial effect, which device is an improvement over the laminated devices associated with the prior art.

Another immediate object of the invention is to provide an osmotic dispenser comprising a wall which possesses the inherent property of self regulating its permeability in response to changes in the fluid environment of use.

Yet another object of the invention is to provide an osmotic device comprising a wall formed of a composition consisting essentially of a semipermeable member and an enteric member for controlling the release of agent from the device.

Still another object of the invention is to provide a composition of matter comprising a semipermeable member and an enteric member which composition is useful for forming the wall of an active agent dispenser.

Still yet another object of the invention is to provide an osmotic dispensing device that can dispense a beneficial agent at a rate, or rates, controlled by the dispenser which are in response to the biological environment within which the dispenser functions over time.

Other objects, features and advantages of the invention will be apparent to those skilled in the art from the detailed description of this specification, taken in conjunction with the drawings and the accompanying claims.

BRIEF DESCRIPTION OF THE DRAWINGS

In the drawings, which are not drawn to scale, but rather are set forth to illustrate various embodiments of the invention, the Figures appear as follows.

DETAILED DESCRIPTION OF THE DRAWINGS

Figure 1:
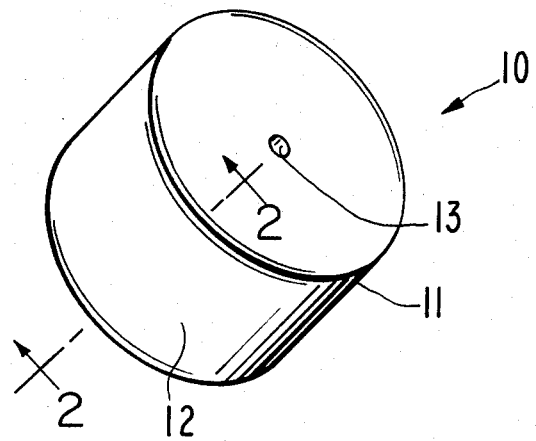
FIG. 1 is a view of an osmotic therapeutic dispenser designed for orally delivering a beneficial drug.
Figure 2:
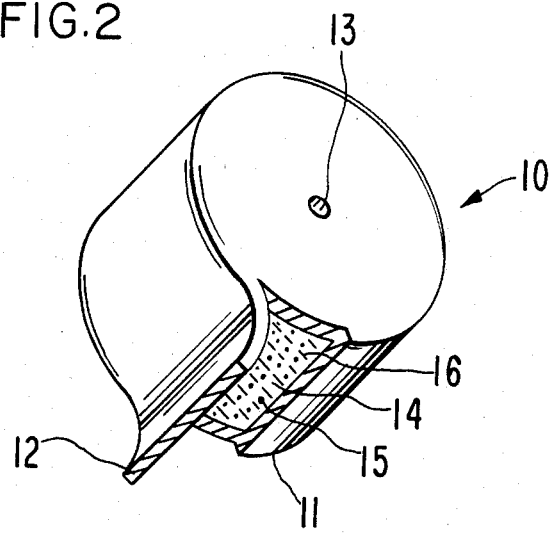
FIG. 2 is a view of the osmotic therapeutic dispenser of FIG. 1 in opened section through 2—2 illustrating the internal compartment of the dispenser.

Turning now to the drawings in detail, which are examples of osmotic dispensers provided by the invention, and which examples are not to be construed as limiting, one embodiment of an osmotic dispenser is seen in FIGS. 1 and 2 indicated by the numeral 10. In FIG. 1, dispenser 10 comprises a body 11 having a wall 12 that surrounds an internal compartment seen in FIG. 2. A passageway 13 in wall 12 connects the interior of osmotic dispenser 10 with the exterior of dispenser 10.

In FIG. 2, osmotic dispenser 10 of FIG. 1 is seen in opened section with a portion of wall 12 cut and turned for illustrating the internal structure of osmotic dispenser 10. Dispenser 10 comprises a composite wall formed of a semipermeable polymer and an enteric agent, which wall surrounds and forms internal compartment 14. Wall 12 of dispenser 10 comprises a semipermeable polymer that is permeable to the passage of an exterior fluid present in the environment of use, substantially impermeable to the passage of drug and other compounds present in compartment 14 or present in the environment of use, and an enteric agent that is substantially insoluble in gastric fluid and is substantially soluble in intestinal fluid. Wall 12 is formed of the composition comprising the semipermeable and enteric materials which materials are nontoxic to a host.

Compartment 14 houses a beneficial drug identified by dots 15 that is preferably soluble in an external fluid that enters compartment 14 and exhibits an osmotic pressure gradient across wall 12 against the external fluid. In another embodiment, drug 15 has limited solubility in the external fluid that enters compartment 14 and it is mixed with an osmotically effective compound 16, identified by dashes, that is soluble in the fluid and exhibits an osmotic pressure gradient across wall 12 against an external fluid. Compartment 14 optionally contains a non-toxic dye for identifying drug 15 and for making release of drug 15 visible to the unaided eye.

Osmotic dispenser 10 releases drug 15 contained in compartment 14 in the gastric region by fluid being imbibed into compartment 14 in a tendency towards osmotic equilibrium at a rate controlled by the permeability of composite, semipermeable-enteric wall 12, and the osmotic pressure gradient across wall 12 to continuously dissolve drug 15, which drug 15 is pumped from dispenser 10 through passageway 13 at a controlled and continuous rate over a prolonged period of time. That is, in the stomach fluid passes through the semipermeable polymer into the compartment to form a solution containing drug that is dispensed from the device into the stomach over time.

Osmotic dispenser 10 releases drug 15 contained in compartment 14 in the intestine by the operation described for the gastric region, and additionally by enteric composition being dissolved or leached from wall 12; thereby, increasing the permeability of the wall 12 and consequently controlling the continuous rate of release of drug 15 in the intestine.

Osmotic dispenser 10 releases drug 15 that has a limited solubility in the fluid and is mixed with an osmotically effective compound by imbibing fluid in the gastric region, or in the intestinal region, through wall 12 into compartment 14, in a tendency towards osmotic equilibrium, at a rate controlled by the permeability of wall 12 and the osmotic pressure gradient across wall 12, to continuously dissolve the osmotically effective compound in compartment 14, and form a solution containing drug 15, that is released from dispenser 10 through passageway 13 at a controlled and continuous rate over a prolonged period of time.

Osmotic dispenser 10 of FIGS. 1 and 2 can be made into many embodiments including the presently preferred embodiments for oral use. The oral system is useful for releasing in the gastrointestinal tract either a locally or a systemically acting drug over a prolonged period of time. Osmotic, oral therapeutic dispenser 10 can have various conventional shapes and sizes such as round with a diameter of ⅛ inches to 9/16 inches, or it can be shaped like a capsule having a range of orally administrable sizes from triple zero to zero, and from 1 to 8, and the like.

Figure 3A:
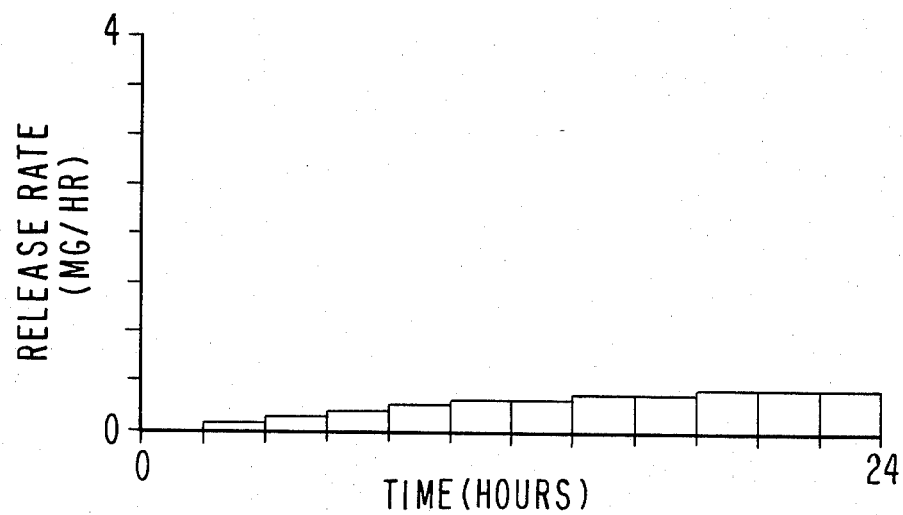
FIG. 3a is a profile of an osmotic dispenser showing its release rate characteristics in an acidic environment of use.
Figure 3B:
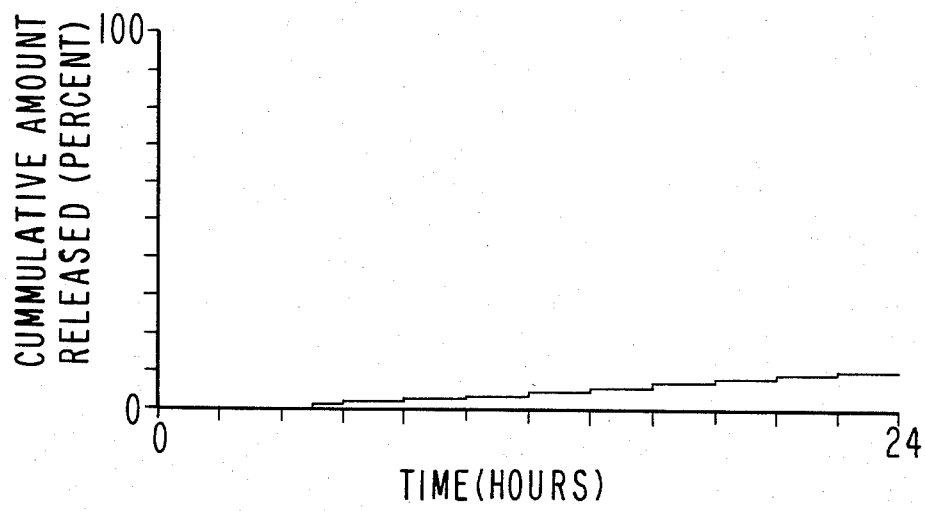
FIG. 3b is a graph illustrating the cumulative amount released in an acidic environment for an osmotic device provided by the invention.
Figure 4A:
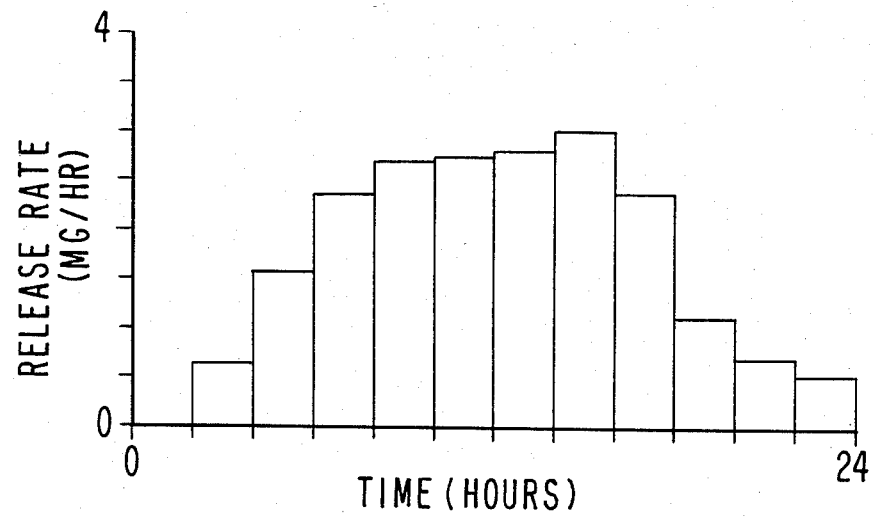
FIG. 4a is a graph depicting the release rate in an alkaline environment for an osmotic device provided by the invention; and, FIG. 4b depicts the cumulative amount released in an alkaline environment for an osmotic device.
Figure 4B:
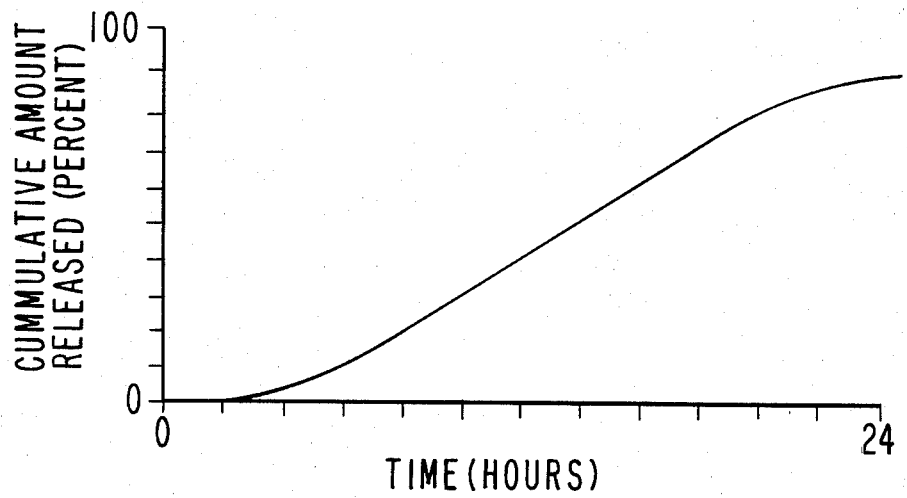

In FIGS. 3a and 3b, release rate of drug versus time and cumulative amount of the drug released versus time are shown for an osmotic dispenser releasing in the acidic environment, such as in gastric fluid present in the stomach. In FIGS. 4a and 4b, the release rate of drug versus time and cumulative amount of the drug released versus time are shown for an alkaline environment, such as in intestinal fluid present in the intestine of the gastrointestinal tract.

While FIGS. 1 and 2 are illustrative of various osmotic dispensers 10 that can be made according to the invention, it is to be understood these dispensers are not to be construed as limitinng, as the dispensers can take a wide variety of shapes, sizees, forms, and performances adapted for delivering different drugs to different biological hosts and biological environments.

DETAILED DESCRIPTION OF THE DRAWINGS

In attaining the objects, features, and advantages of this invention, it has now been found that an osmotic dispenser can be provided for dispensing drug in the gastrointestinal tract comprising the stomach and the intestine according to the mode and the manner of the invention. The osmotic dispenser comprises a wall that surrounds and defines a compartment. The compartment contains a drug, and optionally an osmotically effective solute. There is a passageway in the wall for dispensing drug from the dispenser.

The wall of the osmotic dispenser is formed of a composite consisting essentially of materials that do not adversely affect the drug, the compound, or the biological environment. The wall is formed of a composition comprising a selectively permeable polymeric material and an enteric material that are homogenously, or heterogenously, blended or dispersed in a wall forming intimate operable relation to yield an osmotically functioning wall.

The selectively permeable polymers useful for manufacturing the semipermeable wall of the osmotic dispenser are represented by a member selected from the group consisting essentially of cellulose acylate; cellulose diacylate; cellulose triacylate; cellulose acetate; cellulose diacetate; cellulose triacetate; polyamides; polyurethanes; and the like. Suitable semipermeable polymers for manufacturing osmotic dispensers are disclosed in U.S. Pat. Nos. 3,845,770; 3,916,899; 4,008,719, 4,036,228; and 4,111,210. These patents are assigned to the ALZA Corporation of Palo Alto, Calif., the assignee of this patent application.

The enteric materials that can be blended with the semipermeable polymer for forming the wall of the dispenser are non-toxic enteric materials. The materials and their degradation products should be physiologically inactive, the enteric materials should not dissolve or disintegrate in the stomach during the time the dispenser remains in the stomach, and the enteric materials should disintegrate once the dispenser enters the intestine. The enteric materials suitable for the present invention include those materials digestible by enzymes in the intestinal tract, enteric materials containing an ionizable polyacid, frequently a long-chain polymer with ionizable carboxyl groups, and the like. Typical enteric materials include keratin; keratin sandarac-tolu; salol; salol β-naphthyl benzoate and acetotannin; salol with balsam of peru; salol with tolu; salol with gum mastic; salol and stearic acid; salol and shellac; formalized gelatin; formalized cross-linked gelatin and exchange resins; fatty acids; fats; waxes; fatty acid-wax mixtures; myristic acid-hydrogenated castor oil-cholesterol; stearic acid-mutton tallow; stearic acid-balsam of tolu; stearic acid-castor oil; shellac; ammoniated shellac; ammoniated shellac-salol; shellac-wool fat; shellac-cetyl alcohol; shellac-stearic acid-balsam of tolu; shellac-n-butyl stearate; abietic acid; methyl abietate; benzoin; balsam of tolu; sandarac; mastic with tolu; mastic with cetyl alcohol; cellulose acetate phthalate; cellulose acetate phalate with resinous carrier; cellulose acetate and shellac; starch acetate phthalate; polyvinyl acid phthalate; methylcellulose acid phthalate; hydroxypropyl methylcellulose phthalate; 2-ethoxy-5-(2-hydroxyethoxymethyl)cellulose phthalic acid; acid phthalates of carbohydrates; zein; alkyl resin-unsaturated fatty acids-shellac; hippuric acid; ternary copolymers of styrene; copolymers of methacrylic acid and methylmethacrylate such as methacrylic acid-methylmethacrylate 50:50, and copolymer methacrylic acid-methylmethacrylate 30:70; copolymer hydrolyzed styrene-maleic anhydride; poly(methyl vinyl ether/maleic anhydride); carboxylated copolymer of vinyl acetate; colophony; mixtures of zein and carboxymethylcellulose; methyl cellulose acid phthalate; styrene-maleic acid monoester copolymer; styrene-maleic acid-maleic acid monoester terpolymers; partial esters of isopropyl poly(vinyl methyl ether/-maleic anhydride); half esters of poly(ethylene/maleic anhydride); half esters of poly(vinyl methyl ether/-maleic anhydride); precipitation, association, and polyelectrolyte polymers such as polyacrylic acid blended with polyvinyl pyrrolidone; polyacrylic acid with polyethylene oxide; methylvinyl ether maleic anhydride with polyvinyl pyrrolidone; calcium chloride with poly(acrylamide); aluminum sulfate with poly(acrylamide); amino acids of isoelectric point below pH7 comprising: alanine; aspartic acid; cystine; glutamic acid; glycine; isoleucine; leucine, methionine; phenylalanine; proline; sarconine; serine; threonine; tryptophene; tyrosine; valine; and the like. The amount of enteric material blended with the semipermeable polymer is about 0.5 wt% to 40 wt%. Typical enteric materials are discussed in *Remington's Pharmaceutical Sciences,* Thirteenth Ed., pages 604 to 605, 1965, published by Mack Publishing Co., Eaton, Penna., and in *Biopharmaceutics and Relevant Pharmacokinetics,* First Ed., page 158 to 165, 1971, published by Drug Intelligence Publications, Hamilton, Ill.

The expression passageway as used herein includes an aperture, orifice, bore, hole and the like through the wall. The expression includes also an erodible element in the wall such as a gelatin plug that erodes and forms a passageway in the environment of use. A detailed description of osmotic passageways, and the maximum and minimum dimensions for passageways are disclosed in U.S. Pat. Nos. 3,845,770 and 3,916,899.

Plasticizers are included optionally in the wall formulation to impart flexibility to it and to facilitate the dissolution and subsequent leaching of enterically-active members. Such plasticizers include triethyl citrate; tributyl citrate; tributyrin; butyl phthalyl butyl glycolate; triacetin; triethyl citrate; polyethylene glycol; acetyl triethyl citrate; tributyl citrate; acetyl tributyl citrate; acetyl tri-2-ethylhexyl citrate; sorbitol; glycerin; corn oil, castor oil; cotton seed oil; and the like.

The expression drug as used herein broadly includes any compound, composition of matter, drug formulation, or mixture thereof, that can be delivered from the dispenser to produce a beneficial and useful result. The term drug more specifically includes any substance that produces a local or a systemic effect in animals, avians, pises and reptiles. The term animal includes primates, humans, warm-blooded animals, sport and farm animals, dogs, cats, laboratory animals and the like. The drugs that can be delivered by the method of the invention include inorganic and organic drugs, such as central nervous system acting drugs, hypnotics, sedatives, psychic energizers, tranquilizers, antisteroids, laxatives, antideprressants, anti-convulsants, muscle relaxants, antiparkinson agents, anesthetics, antiinflammatory agents, antimalarials, hormones, sympathomimetics, antibiotics, diuretics, antiparasitics, neoplastics, hypoglycemics, nutritionals, and the like. Representative of specific drugs include aminobarbital, aminophylline, aminosalicylic acid, ammonium biphosphate, ammonium chloride, amylase, anti-histamine, aspirin, atropine sulfate, avazyme, choledyl, chymoral, chymoral-100, chymotrypsin, diasone sodium, diethylstilbestrol, E-mycin, erythromycin, ephedrine hydrochloride, ferrous sulfate, gentian violet, hemicellulase, hydralazine, hyoscine hydrobromide, hyoscyamine sulfate, ilotycin, lipase, methenamine mandelate, orenzyme, ox-bile extract, oxtriphylline, pancreatin, papain, phenobarbital, potassium chloride, potassium iodide, potassium thlocyanate, quinidine sulfate, robimycin, sodium aminobenzoate, sodium biphosphate, sodium chloride, sodium salicylate, sodium secobarbital, stilbestrol, stilbetin, sulfasalazine, thyroid, and urethan. The amount of drug present in a dispenser will vary depending on the activity and the amount of drug to be administered to the host. Generally, the osmotic dispenser will be from 0.05 mg to 3 g or more, with individual dispensers containing for example 5 mg, 25 mg, 50 mg, 125 g, 250 mg, 500 mg, and the like. The drug can be in the dispenser in various forms such as dispersion, granule, powder, pressed mass, film, and the like. The beneficial drugs and their present doses are known to the dispensing art in *Pharmaceutical Sciences,* by Remington, 15th Ed., 1975, published by Mack Publishing Co., Easton, PA; *The Drug, The Nurse, The Patient Including Current Drug Handbook,* 1974–1976, by Falconer, et al., published by Saunder Company, Philadelphia, PA; in *Physician Desk Reference,* 33rd Ed., 1979, published by Medical Economics, Oradell, NJ, in *Ann. of Allergy,* Vol. 41, pages 75 to 77, 1979; in *Arzneim. Forsch.,* Vol. 25, pages 1629 to 1935, 1975; and in *J. Inter. Med. Res.,* Vol. 7, pages 335 to 338, 1979.

The expression "osmotically effective compound" as used herein, includes inorganic and organic compounds that are effective solutes that exhibit an osmotic pressure gradient across the wall of the dispenser against an external fluid. The osmotic solutes are conveniently used by homogenously or heterogenously mixing a solute with the active drug in the compartment of the dispenser. In operation, these solutes osmotically attract fluid into the dispenser to produce a solution of the solute which is osmotically released from the device concomitantly transporting therewith dissolved and undissolved drug. Various osmotically effective solutes include compounds such as magnesium sulfate, magnesium chloride, sodium chloride, lithium chloride, potassium sulfate, sodium sulfate, potassium chloride, potassium acid, mannitol, urea, inositol, magnesium succinate, raffinose, sucrose, glucose, and the like. The osmotic solute preferably is initially in excess, and it can be in any suitable physical form such as particles, crystals, pellets, granules, and the like. The amount of osmotic solute in a dispenser is about from 0.5 mg to 500 mg, or more.

The osmotic dispenser of the invention is manufactured by standard techniques. For example, in one embodiment, the drug is mixed with other ingredients by ballmilling, calendering, stirring, and pressing into a preselected shape. The materials forming the wall and blended into a composition and applied by dipping, molding, or spraying the pressed drug core. One procedure for applying the wall is the air suspension technique. The air suspension technique can be used for manufacturing a wall as described in U.S. Pat. No. 2,799,341; in *J. Am. Pharm. Assoc.* Vol. 48, pages 451 to 459, 1959; and *J. Am. Pharm. Assoc.* Vol. 49, pages 82 to 84, 1960.

The solvents used for forming the wall include water, ketones, esters, ethers, alcohols, aliphatic hydrocarbons, halogenated solvents, cycloaliphatics, aromatics, heterocyclic solvents, and mixtures thereof. Typical solvents include acetone, diacetone, methanol, ethanol, isopropyl alcohol, methyl isobutyl ketone, n-heptane, methylene, dichloride, ethylene dichloride, mixtures such as acetone and water, ethanol and water, acetone and ethyl alcohol, methylene dichloride and methanol, ethylene dichloride and methanol, and the like.

The following example is merely illustrative of the present invention, and it should not be considered as limiting the scope of the invention in any way, as this example and other equivalents thereof will become apparent to those versed in the art in the light of the present disclosure, the drawings and the accompanying claims.

EXAMPLE

An osmotic dispenser for the delivery of the beneficial drug hydralazine hydrochloride is manufactured as follows: a drug formulation is prepared for housing in the compartment of the dispenser by forming drug cores weighing 275 mg and consisting of the drug present as 18.2 wt% hydralazine hydrochloride, 75.9 wt% mannitol, 2.9 wt% hydroxypropyl methylcellulose, and 3 wt% stearic acid, which were blended into a homogenous formulation and a precompartment formed by compressing the mass in a ⅜ inch standard concave punch in a Manesty press at 1.5 ton pressure head.

Next, the compressed drug core is placed in an air suspension coating machine and coated with a semipermeable-enteric composition consisting of 35 wt% cellulose acetate having an acetyl content of 39.8%, 35 wt% cellulose acetate having an acetyl content of 32.0%, with an enteric composition consisting of 15 wt% hydroxypropyl methyl cellulose phthalate grade 50 and 15 wt% triacetin. This composition is applied from a solution of 5 wt% solids in a solvent system consisting essentially of 1900 g methylene chloride and 1900 g methanol. The dispensers are coated to a wall weight of approximately 19 mg and are dried in an air oven at 50° C. A 10 mil passageway is laser drilled through the wall to complete fabrication of the osmotic dispenser.

In FIG. 3a, the dispenser is shown releasing in gastric fluid at an average rate of approximately 0.5 mg/hr. The measured delivery rate of this dispenser, as depicted in FIG. 4a, when operating in intestinal fluid rises six fold to a rate of approximately 3 mg/hr. The cumulative rate in gastric fluid is seen in FIG. 3b, and the cumulative rate in intestinal fluid is seen in FIG. 4b.

Systems identical to these but manufactured with non-enteric members consisting of 15 wt% hydroxypropyl methylcellulose grade 606 and 15 wt% polyethylene glycol 4000 grade 4000 substituted for the enteric composition in this cellulose acetate wall release in gastric fluid and in intestinal fluid at the same rate.

I claim:

1. An oral osmotic therapeutic dispenser for the controlled dispensing of a drug formulation in the gastrointestinal tract, which dispenser comprises:
    (a) a shaped osmotically functioning wall formed of a composition consisting essentially of (i) a selectively semipermeable material permeable to the passage of fluid, substantially impermeable to the passage of drug, which maintains its physical and chemical integrity in the presence of gastric fluid and intestinal fluid, and is a member selected from the group consisting of cellulose acylate, cellulose diacylate, cellulose triacylate, cellulose acetate, cellulose diacetate, and cellulose triacetate, blended with (ii) from 0.5 wt.% to 40 wt.% of an enteric material that is substantially insoluble in gastric fluid, leaves the shaped wall in response to intestinal fluid, thereby increasing the passage of fluid through the shaped wall in the intestine while maintaining the osmotic functionality of said shaped wall wherein the wall remains substantially impermeable to the passage of the drug, the wall surrounding and forming:
    (b) a compartment containing from 0.05 mg to 3 g of a drug formulation that is soluble in external fluid that enters the compartment and exhibits an osmotic pressure gradient across the wall against an external fluid when the dispenser is in the gastrointestinal tract;
    (c) an osmotic passageway in the wall communicating with the compartment and the exterior of the osmotic dispenser for dispensing drug formulation from the dispenser; and,
    (d) wherein, when the osmotic dispenser is in the gastrointestinal tract, fluid passes through the wall of the osmotic dispenser into the compartment to continuously dissolve the drug formulation to create an osmotic pressure within the device whereby the formulation is osmotically delivered through the passageway at a controlled rate over a prolonged period of time to the gastrointestinal tract.

2. The osmotic therapeutic dispenser for the controlled delivery of drug formulation according to claim 1, wherein the drug formulation comprises an osmotically effective solute.

* * * * *